United States Patent [19]

Shephard et al.

[11] 4,130,409

[45] Dec. 19, 1978

[54] TRIAZOLYL BUTANDIONES

[75] Inventors: Margaret C. Shephard; Paul A. Worthington, both of Maidenhead, England

[73] Assignee: Imperial Chemical Industries Limited, London, England

[21] Appl. No.: 802,545

[22] Filed: Jun. 1, 1977

[30] Foreign Application Priority Data

Jun. 8, 1976 [GB] United Kingdom ............... 23601/76
Sep. 3, 1976 [GB] United Kingdom ............... 36614/76
Feb. 8, 1977 [GB] United Kingdom ................. 5140/77

[51] Int. Cl.² .................. A01N 9/22; A01N 21/02; A61K 31/41; C07D 249/08
[52] U.S. Cl. .............................. 71/76; 71/92; 260/299; 260/308 R; 424/245; 424/269
[58] Field of Search ..................... 260/308 R, 299; 424/269; 71/76, 92

[56] References Cited

U.S. PATENT DOCUMENTS 3,912,752 10/1975 Meiser et al. ............... 424/269
3,972,892 8/1976 Büchel et al. ............... 424/269

Primary Examiner—Alton D. Rollins
Attorney, Agent, or Firm—Cushman, Darby & Cushman

[57] ABSTRACT

Compounds of formula:

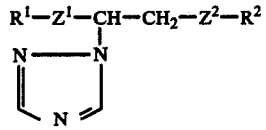

wherein $R^1$ and $R^2$ are alkyl, cycloalkyl or phenyl and $Z^1$ and $Z^2$ are carbonyl or a derivative thereof, or salts or metal complexes thereof. They have fungicidal and plant growth regulating activity.

21 Claims, No Drawings

TRIAZOLYL BUTANDIONES

This invention relates to triazole compounds useful as fungicides and plant growth regulating agents, to a process for preparing them, to fungicidal and plant growth regulating compositions containing them, to a method of combating fungal infections in plants using them and to a method of regulating the growth of plants using them.

The triazole compounds have the general formula (I)

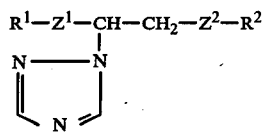

wherein each of $R_1$ and $R_2$, which may be the same or different, is unsubstituted or alkyl-substituted cycloalkyl (e.g. cyclopentyl, cyclohexyl or methylcyclohexyl), unsubstituted or halo-substituted alkyl (e.g. trichloromethyl) or unsubstituted or halo-, alkyl-, alkoxy- or nitro-substituted phenyl, and each of $Z^1$ and $Z^2$, which may be the same or different, is C=O or a derivative thereof (e.g. an imine, oxime, ketal, hydrazone or semicarbazone); or an acid addition salt or metal complex thereof.

The compounds of the invention contain chiral centres. The compounds are generally obtained in the form of racemic mixtures. However, these and other mixtures can be separated into the individual isomers by methods known in the art.

The alkyl and alkoxy groups can be straight or branched chain groups having 1 to 10, e.g. 1 to 6 carbon atoms; examples are methyl, ethyl, propyl (n- or iso-propyl), butyl (n-, iso- or t-butyl), methoxy and ethoxy. The halogen atoms can be fluorine, chlorine, bromine, or iodine. Examples of the substituted phenyl groups are p-tolyl or o-, m- or p-chloro-, o-, m- or p-fluoro-, 4-nitro, or 2,4- or 2,6-dichlorophenyl. The phenyl group can be substituted with up to the maximum possible number of halogen (particularly chlorine) atoms and/or nitro groups.

The salts can be salts with inorganic or organic acids e.g. hydrochloric, nitric, sulphuric, acetic or oxalic acid.

Suitably the metal complex is one including, as the metal, copper, zinc, manganese or iron. It preferably has the general formula:

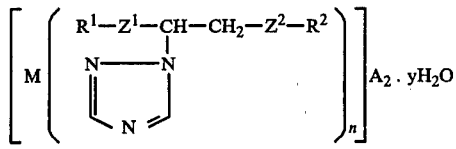

wherein $R^1$, $R^2$, $Z^1$ and $Z^2$ are as defined above, M is a metal, A is an anion (e.g. a chloride, bromide, iodide, nitrate, sulphate or phosphate anion), n is 2 or 4 and y is 0 or an integer of 1 to 12.

Examples of the compounds of the invention are shown in Table I.

TABLE I

| Compound No | $R^1$ | $R^2$ | $Z^1$ | $Z^2$ | Melting Point (°C) |
|---|---|---|---|---|---|
| 1 | $C_6H_5$ | $C_6H_5$ | C=O | C=O | 193–194° |
| 2 | p-Cl—$C_6H_4$ | p-Cl—$C_6H_4$ | C=O | C=O | 151–153° |
| 3 | t-Bu | t-Bu | C=O | C=O | 66–69° |
| 4 | t-Bu | $C_6H_5$ | C=O | C=O | 117–118° |
| 5 | p-Me—$C_6H_4$ | p-Me—$C_6H_4$ | C=O | C=O | 193–195° |
| 6 | t-Bu | p-Cl—$C_6H_4$ | C=O | C=O | 121–123° |
| 7 | i-Pr | p-Cl—$C_6H_4$ | C=O | C=O | 82–83° |
| 8* a | t-Bu | p-F—$C_6H_4$ | C=O | C=O | oil |
| 8* b | p-F—$C_6H_4$ | t-Bu | C=O | C=O | oil |
| 9 | Me | $C_6H_5$ | C=O | C=O | 99–101° |
| 10 | Me | p-Cl—$C_6H_4$ | C=O | C=O | 106–109° |
| 11 | Me | p-F—$C_6H_4$ | C=O | C=O | 103–105° |
| 12 | cyclohexyl | p-Cl—$C_6H_4$ | C=O | C=O | 93–96° |
| 13 | Et | p-Cl—$C_6H_4$ | C=O | C=O | 90–92° |
| 14 | n-Pr | p-Cl—$C_6H_4$ | C=O | C=O | 77–79° |
| 15 | n-Bu | p-Cl—$C_6H_4$ | C=O | C=O | 81–82° |
| 16 | p-F—$C_6H_4$ | p-F—$C_6H_4$ | C=O | C=O | 115–116° |

*A mixture of 70% by weight of Compound 8a and 30% by weight of Compound 8b

The triazole compounds may be made by reacting 1,2,4-triazole, or a salt or metal complex thereof, and the appropriate δ-diketone, by any of the methods set out in the literature. Thus 1,2,4-triazole can be reacted with a compound (e.g. a δ-diketone) of general formula (II)

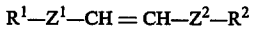

$$R^1-Z^1-CH=CH-Z^2-R^2$$

wherein $R^1$, $R^2$, $Z^1$ and $Z^2$ are as defined above.

Sometimes this process can be carried out merely by heating the reactants together in the absence of a solvent or diluent, but preferably a solvent is present. Suitable solvents are high-boiling hydrocarbon solvents such as benzene, toluene or a xylene.

The process is generally performed by dissolving the reactants in a solvent and, after allowing reaction to occur, isolating the product by removing the solvent in vacuo. Any untreated triazole can be removed by extraction with a suitable solvent and the extract can then be washed with water. Crystallisation or other purification procedures may then be carried out, if desired.

The δ-diketone starting material may be made by methods set out in the literature.

The salts and metal complexes of the compounds of general formula (I) can be prepared in known manner. For example, the complexes can be made by reacting the uncomplexed compound with a metal salt in a suitable solvent.

The compounds are active fungicides, particularly against the diseases:
Piricularia oryzae on rice
*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants
*Plasmopara viticola* on vines
*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines
*Botrytis cinerea* (grey mould) on tomatoes, strawberries, vines and other hosts
*Phytophthora infestans* (blight) on tomatoes
Venturia inaequalis (scab) on apples
Some of the compounds have also shown a broad range of activities against fungi in vitro. Further some of the compounds are active as seed dressings against: Fusarium spp., Septoria spp., Tilletia spp., Ustilago spp., and Pyrenophora spp. on cereals.

The compounds also have plant growth regulating activities.

The plant growth regulating effects of the compounds are manifested as for example as stunting or dwarfing effect on the vegetative growth of mono- and di-cotyledonous plants. Such stunting or dwarfing may be useful, for example, in cereals and soya bean where reduction in stem growth may reduce the risk of lodging. Compounds which induce stunting or dwarfing may also be useful in stunting the growth of sugar cane thereby increasing the concentration of sugar in the cane at harvest. Stunting of peanuts can assist in harvesting. Growth retardation of grasses can help maintenance of grass swards. The plant growth regulating effect may manifest itself in an increase in crop yield.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. The treatment of plants with the compounds of the invention can lead to the leaves developing a darker green colour.

Further the compounds may inhibit the flowering of sugar beet and thereby may increase sugar yield.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15 kg per hectare is used. However, on certain plants even application rates within these ranges may give undesired phytotoxic effects. Routine tests may be necessary to determine the best rate of application of a specific compound for any specific purpose for which it is suitable.

The compounds also have herbicidal activity.

The compounds may be used as such for fungicidal or plant growth regulating purposes but are more conveniently formulated into compositions for such usage. The invention thus provides also a fungicidal or plant growth regulating composition comprising a compound of general formula (I) or a salt or complex thereof as hereinbefore defined, and a carrier or diluent.

The invention also provides a method of combating fungal diseases in a plant, which method comprises applying to the plant, to seed of the plant or to the locus of the plant or seed a compound or salt or complex thereof as hereinbefore defined.

It also provides a method of regulating the growth of a plant, which method comprises applying to the plant, to seed of the plant or to the locus of the plant or seed a compound or salt or complex thereof as hereinbefore defined.

The compounds, salts and complexes can be applied in a number of ways, for example they can be applied, formulated or unformulated, directly to the foliage of a plant which is infected or likely to become infected, or they can be applies also to bushes and trees, to seeds or to other medium in which plants, bushes or trees are growing or are to be planted, or they can be sprayed on, dusted on or applied as a cream or paste formulation or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed. Alternatively the active ingredient can be formulated for seed dressing purposes using an organic solvent (for example N-methylpyrrolidone or dimethylformamide).

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent (s). Suitable organic solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive powder and resistance to rain on treated surfaces, the different compositions can be better adapted for various utilities.

The compounds can be used as mixtures with fertilisers (e.g. nitrogen — or phosphorus — containing fertilisers). Compositions comprising only granules of fertiliser incorporating, for example coated with, the compound, are preferred. The invention therefore also provides a fertiliser composition comprising the compound of general formula (I) or a salt or complex thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10-85%, generally 25-60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity (e.g. other growth stimulating substances such as the gibberellins and other compounds having complementary fungicidal or insecticidal activity), as well as stabilising agent(s), for example epoxides (e.g. epichlorhydrin). The other fungicidal compound can be one which is capable of combating ear diseases of cereals (e.g. wheat) such as Septoria, Gibberella, Helminthosporium and the sooty mould complex.

The following Examples illustrate the invention; the temperatures are given in degrees Centigrade (° C.).

EXAMPLE 1

2-(1,2,4-Triazol-1-yl)-1,4-(di-p-chlorophenyl)-butane-1,4-dione (Compound 2)

Stage 1: Chlorobenzene (0.4 mol) and aluminium chloride (0.5 mol) in carbon disulphide (30 ml) were stirred at 50°-60°. Fumaryl chloride (0.2 mol) was added dropwise at a brisk rate over 30 minutes and refluxing was continued for a further 15 minutes. The residue was poured into crushed ice (1 kg) and concentrated hydrochloric acid (15.0 ml). The semi-solid was filtered off, washed with ether and ethanol, and recrystallised from ethyl acetate/ethanol to give pale yellow needles of di-(p-chlorobenzoyl) ethylene m.p. 175°-176°. Analysis:

$C_{16}H_{10}O_2Cl_2$ Requires: C, 63.0%; H, 3.3% Found: C, 62.7%; H, 3.3%

Stage 2: Di-(p-chlorobenzoyl)ethylene (0.026 mol) and 1,2,4-triazole (0.026 mol) were suspended in toluene (150 ml) and refluxed for 6 hours. On cooling to room temperature, a solid crystallised out. It was filtered off and recrystallised from ethyl acetate to give the title compound as a white crystalline solid, m.p. 151°-153°. Analysis:

$C_{18}H_{13}Cl_2N_3O_2$ Requires: C, 57.77%; H, 3.50%; N, 11.23%. Found: C, 57.80%; H, 3.61%; N, 11.45%.

EXAMPLE 2

4-(1,2,4-triazol-1-yl)-2,2,7,7-tetramethyl-octan-3,6dione (Compound 3)

Stage 1: 2,2,7,7-tetramethyl-oct-4-en-3,6-dione, m.p. 107°-9°, was prepared according to the method of Ramasseul and Rassat, Bull. Soc. Chim. Fr., 1963, p 2214-2217.

Stage 2: 2,2,7,7-oct-4-en-3,6-dione (0.01 mol) and 1,2,4-triazole (0.01 mol), suspended in toluene (100 ml), were refluxed for 24 hours. On cooling to room temperature, the organic layer was washed with water (4 × 100 ml) and dried over sodium sulphate. Removal of the solvent gave a white solid which was recrystallised from petroleum ether (60-80) to give the title compound, m.p. 66°-69°.

EXAMPLE 3

The triazole compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by beadmilling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test with *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:

4 = No disease
3 = 0-5%
2 = 6-25%
1 = 26-60%
0 = >60%

The results are shown in Table II.

TABLE II

| Compound No | Puccinia recondita in wheat | Phytophthora infestans in tomato | Plasmopara viticola in vines | Piricularia oryzae in rice | Botrytis cinerea in tomato | Erysiphe graminis in barley |
|---|---|---|---|---|---|---|
| 1 | 1 | 0 | 0 | 0 | 2 | 2 |
| 2 | 0 | 0 | 0 | 0 | 0 | 4 |
| 3 | 4 | 0 | 0 | 0 | 3 | 4 |
| 4 | 3 | 0 | 0 | 0 | 0 | 4 |
| 5 | 0 | 0 | 0 | 0 | 2 | 0 |
| 6 | 0 | 2 | 2 | 3 | 3 | 4 |
| 7 | 2 | 2 | 0 | 2 | 0 | 3 |
| 8 | 4 | 0 | 3 | 2 | 0 | 4 |
| 9 | 0 | 0 | 0 | 0 | 0 | 4 |
| 10 | 0 | 2 | 0 | 1 | 0 | 4 |
| 11 | 0 | 0 | 0 | 1 | 0 | 4 |
| 12 | 0 | 0 | 0 | 0 | 1 | 4 |
| 13 | 1 | 0 | 4 | 0 | 0 | 4 |
| 14 | 1 | 1 | 0 | 0 | 0 | 3 |
| 15 | | | | | | |
| 16 | | | | | | |

EXAMPLE 4

This Example illustrates the plant growth regulating properties of the compounds. The compounds were applied in the form of a 5000 ppm solution in distilled water and the solution was then applied to the foliage of young seedlings of wheat, barley, maize, rice, Lolium ryegrass, soya, cotton, groundnut, lettuce, tomato, Mung bean and French bean. The experiments were replicated twice. After 21 days from treatment, the plants were assessed for plant growth regulating effects and phytotoxic symptoms.

Table III shows the stunting effect of the compounds on the vegetative growth using the following grading:

0 = ≦20% retardation
1 = 21–40% retardation
2 = 41–60% retardation
3 = 61–80% retardation If no figure is given, the compound was substantially inactive as a stunting agent. Additional plant growth regulating properties are indicated as follows:

G = darker green leaf colour
A = apical effect
T = tillering effect

The symbol "—" is used to indicate that the compound has not been tested on that particular crop.

TABLE III

| Compound | Wheat | Barley | Maize | Rice | Lolium Ryegrass | Soya | Cotton | Ground Nut | Lettuce | Tomato | Mung Bean | French Bean |
|---|---|---|---|---|---|---|---|---|---|---|---|---|
| 1 | 0 | | | | | | | 0 | | 0G | | 0GA |
| 2 | 0 | 0 | 0 | | | | 0 | 1 | | 1G | | 1GA |
| 3 | — | — | — | — | — | — | — | — | — | — | — | — |
| 4 | 0 | 0 | | | | 0G | 1 | 3 | | 1 | | 1G |
| 5 | 0 | 0 | | | | 0 | 0 | 1 | | 0 | | 2GA |
| 6 | 1G | 1G | | Dying | | 1G | 1 | 2G | 2G | 1AT | 1 | 1GA |
| 7 | — | — | — | — | — | — | — | — | — | — | — | — |
| 8 | 2G | 2 | 1 | Dying | 0 | 2G | 0 | 2 | 2A | 1 | Dead | 2A |
| 9 | | | | | | G | 0 | | G | A | A | 1A |
| 10 | | | | | 1GA | 0 | | | | | | GA |
| 11 | | | | | 0 | | 1 | | | GA | | |
| 12 | — | — | — | — | — | — | — | — | — | — | — | — |
| 13 | 1GT | 1G | | | | A | | | | 1T | A | GA |
| 14 | | | | | | | | | | | | |
| 15 | | | | | | | | | | | | |
| 16 | | | | | | | | | | | | |

We claim:

1. A compound of the formula:

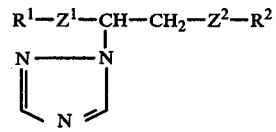

$$R^1-Z^1-CH-CH_2-Z^2-R^2$$

with the CH bearing a 1,2,4-triazol-1-yl group (N—N, N ring)

wherein each of $R^1$ and $R^2$, which may be the same or different, is unsubstituted for $C_1-C_{10}$ alkyl-substituted cyclopentyl or cyclohexyl unsubstituted or halo-substituted $C_1-C_{10}$ alkyl or unsubstituted or halo-, $C_1-C_{10}$ alkyl-, $C_1-C_{10}$ alkoxy- or nitro-substituted phenyl, and each of $Z^1$ and $Z^2$, which may be the same or different, is C═O or an acid addition salt or copper, zinc, manganese or iron complex thereof.

2. A compound as claimed in claim 1 wherein $R^1$ is methyl, ethyl, n-propyl, i-propyl, n-butyl, t-butyl, cyclohexyl, phenyl, p-chlorophenyl, p-fluorophenyl or p-tolyl.

3. A compound as claimed in claim 1 wherein $R^2$ is t-butyl, phenyl, p-chlorophenyl, p-fluorophenyl or p-tolyl.

4. 4-(1,2,4-Triazol-1-yl)-2,2,7,7-tetramethyloctan-3,6-dione.

5. 4-(1,2,4-Triazol-1-yl)-2,2-dimethyl-6-p-chlorophenyl-hexan-3,6-dione.

6. 4-(1,2,4-Triazol-1-yl)-2,2-dimethyl-6-p-fluorophenyl-hexan-3,6-dione.

7. 5-(1,2,4-Triazol-1-yl)-2,2-dimethyl-6-p-fluorophenyl-hexan-3,6-dione.

8. A fungicidal or plant growth regulating composition, the composition consisting essentially of a fungicidally or plant growth regulatingly effective amount of, as active ingredient, a compound, salt or metal complex as claimed in claim 1, and a carrier for the active ingredient.

9. A fungicidal or plant growth regulating composition, the composition consisting essentially of a fungicidally or plant growth regulatingly effective amount of, as active ingredient, a compound as claimed in claim 2, and a carrier for the active ingredient.

10. A fungicidal or plant growth regulating composition, the composition consisting essentially of a fungicidally or plant growth regulatingly effective amount of, as active ingredient, a compound as claimed in claim 3, and a carrier for the active ingredient.

11. A fungicidal or plant growth regulating composition, the composition consisting essentially of a fungicidally or plant growth regulatingly effective amount of, as active ingredient, a compound as claimed in claim 4, and a carrier for the active ingredient.

12. A fungicidal or plant growth regulating composition, the composition consisting essentially of a fungicidally or plant growth regulatingly effective amount of, as active ingredient, a compound as claimed in claim 5, and a carrier for the active ingredient.

13. A fungicidal or plant growth regulating composition, the composition consisting essentially of a fungicidally or plant growth regulatingly effective amount of, as active ingredient, a compound as claimed in claim 6, and a carrier for the active ingredient.

14. A fungicidal or plant growth regulating composition, the composition consisting essentially of a fungicidally or plant growth regulatingly effective amount of, as active ingredient, a compound as claimed in claim 7, and a carrier for the active ingredient.

15. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound, salt or metal complex as claimed in claim 1.

16. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound as claimed in claim 2.

17. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound as claimed in claim 3.

18. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound as claimed in claim 4.

19. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound as claimed in claim 5.

20. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound as claimed in claim 6.

21. A method of combating fungal diseases in, or regulating the growth of, a plant, the method consisting essentially of the step of applying to the plant, to seed of the plant or to the locus of the plant or seed, a fungicidally or plant growth regulatingly effective amount of a compound as claimed in claim 7.

* * * * *